United States Patent
Peng

(10) Patent No.: US 9,778,026 B1
(45) Date of Patent: Oct. 3, 2017

(54) LIGHT PATTERN-BASED INDOOR POSITIONING METHOD

(71) Applicant: HUAZHONG UNIVERSITY OF SCIENCE AND TECHNOLOGY, Wuhan, Hubei (CN)

(72) Inventor: Guo Peng, Hubei (CN)

(73) Assignee: Huazhong University of Science and Technology, Wuhan, Hubei (CN)

( * ) Notice: Subject to any disclaimer, the term of this patent is extended or adjusted under 35 U.S.C. 154(b) by 0 days.

(21) Appl. No.: 15/187,391

(22) Filed: Jun. 20, 2016

(30) Foreign Application Priority Data

Apr. 5, 2016 (CN) .......................... 2016 1 0206961

(51) Int. Cl.
| | | |
|---|---|---|
| *G01B 11/14* | (2006.01) | |
| *G01B 11/26* | (2006.01) | |
| *G06T 7/60* | (2017.01) | |
| *G01B 11/25* | (2006.01) | |
| *G01N 21/956* | (2006.01) | |

(52) U.S. Cl.
CPC .............. *G01B 11/14* (2013.01); *G01B 11/26* (2013.01); *G01B 11/25* (2013.01); *G01B 11/2513* (2013.01); *G01N 21/956* (2013.01); *G06T 7/60* (2013.01)

(58) Field of Classification Search
CPC ......... G01B 11/14; G01B 11/25; G01B 11/26; G01B 11/2433; G01B 11/2545; G01B 21/20; G01N 21/956
See application file for complete search history.

(56) References Cited

U.S. PATENT DOCUMENTS

| | | | | |
|---|---|---|---|---|
| 3,070,173 | A * | 12/1962 | Toulmin, Jr. .......... | B64C 11/301 318/480 |
| 5,854,682 | A * | 12/1998 | Gu ..................... | G01N 21/6447 356/426 |
| 6,191,857 | B1 * | 2/2001 | Meier ................ | G01B 11/2433 356/613 |
| 6,455,835 | B1 * | 9/2002 | Bernardini ............. | G06T 7/564 250/208.1 |
| 9,372,077 | B2 * | 6/2016 | Fleming ................ | G01B 11/02 |

* cited by examiner

*Primary Examiner* — Kara E Geisel
*Assistant Examiner* — Jarreas C Underwood
(74) *Attorney, Agent, or Firm* — Hamre, Schumann, Mueller & Larson, P.C.

(57) ABSTRACT

A light pattern-based indoor positioning method includes the following steps of: (1) setting a light pattern transmitting device; (2) detecting a light signal of the target to be positioned; and (3) positioning the position of the target to be positioned, to obtain a distance ρ from the target to be positioned to the rotating shaft of the blade, and a deflection angle θ of the target to be positioned relative to the reference line.

6 Claims, 1 Drawing Sheet

LIGHT PATTERN-BASED INDOOR POSITIONING METHOD

TECHNICAL FIELD

The present invention relates to the field of IT information technologies, and in particular, to a light pattern-based indoor positioning method, the method having high positioning precision.

BACKGROUND ART

Indoor positioning often requires higher precision. The existing indoor positioning methods are mainly divided into two categories: radio signal-based positioning methods, and light signal-based positioning methods.

For the radio signal-based positioning methods, representative solutions at present are: a distance measurement information-based positioning method, a detection area-based positioning method, and a radio geographical distribution prior knowledge-based positioning method. The methods have a common disadvantage: as a radio signal is easily affected by an environment, positioning reference provided is not stable, thus leading to lower positioning precision.

For the light signal-based positioning methods, representative solutions at present are: specific optical characteristic of a target to be positioned-based positioning method, and a fixed reference object specific optical characteristic-based positioning method. The former has a specific requirement for a hardware function of a target to be positioned, the latter has a specific requirement for deployment of a fixed reference object, and thus both lead to obstacles to application popularization. In addition, the methods have a smaller positioning scale (including the number of targets to be positioned, the size of the positioning range and the like), which also limits their application ranges.

SUMMARY

With respect to the above defects or improvement demands of the prior art, an objective of the present invention is to provide a light pattern-based indoor positioning method, which, by making improvements to composition and setting of a key light pattern transmitting device thereof, measurement parameters of the corresponding light pattern-based indoor positioning method and the like, can effectively solve the problem that indoor positioning precision is not high as compared with the prior art, the indoor positioning method can achieve centimeter-level positioning precision, has a great number of targets to be positioned, and has a wide positioning range; in addition, the indoor positioning method has low requirements for hardware functions of the targets to be positioned, which can greatly expand an application range.

In order to achieve the above objective, according to one aspect of the present invention, a light pattern-based indoor positioning method is provided, including the following steps of:

(1) setting a light pattern transmitting device:

the light pattern transmitting device including a light source, a blade and a motor, wherein the blade is connected with the motor, the motor drives the blade to make the blade rotate at a constant speed around a rotating shaft of the blade; a straight line where the rotating shaft of the blade is located passes through the center of the light source, and the rotating shaft is perpendicular to the ground; light emitted by the light source is blocked by the blade to form a shadow on the ground, and the shadow rotates periodically along with the blade to form a periodic light pattern; on a ground area covered periodically by the shadow, within the time of one cycle of rotation of the blade, the duration during which points on the ground area at different distances from the rotating shaft of the blade are kept to be covered by the shadow due to the periodic light pattern is different; a target to be positioned is located on the ground, and is covered periodically by the shadow; and the light source flashes periodically, and the cycle of the periodic flashing is the same as the cycle of rotation of the blade;

(2) detecting a light signal of the target to be positioned:

detecting light signal intensity received by the target to be positioned through a photosensitive sensor; within the time of one cycle of rotation of the blade, when the photosensitive sensor detects that the light signal intensity changes due to the periodic flashing of the light source, denoting the time as a reference time, and denoting a projection of a straight line passing through any two points on the blade on the ground at the reference time as a reference line, wherein the straight line passing through any two points on the blade and the straight line where the rotating shaft is located intersect with but do not coincide with each other;

(3) positioning the position of the target to be positioned:

according to changes of the light signal intensity with the periodic light pattern detected by the photosensitive sensor, judging a distance ρ from the target to be positioned to the rotating shaft of the blade, and a deflection angle θ of the target to be positioned relative to the reference line.

As a further optimization of the present invention, if the cycle of rotation of the blade is denoted as T, within the time of one cycle of rotation of the blade, the time at which the light signal intensity detected by the photosensitive sensor changes from strong to weak due to the periodic light pattern is denoted as a changing time, and the time at which the changing time lags behind the reference time is denoted as T', the angle θ of the target to be positioned relative to the reference line satisfies: θ=2π(T'/T).

According to another aspect of the present invention, a light pattern-based indoor positioning method is provided, including the following steps of:

(1) setting a light pattern transmitting device:

the light pattern transmitting device including a light source, a blade and a motor, wherein the blade is preferably a diamond, the plane where the diamond is located is parallel to the ground, the length of the long diagonal of the diamond is denoted as 2×R, and the length of the short diagonal of the diamond is denoted as D;

the motor drives the blade to make the blade rotate at a constant speed, a connecting line between the center of the light source and the center of the blade is perpendicular to the ground, light emitted by the light source is blocked by the blade to form a shadow on the ground, and the shadow rotates periodically along with the blade to form a periodic light pattern; a target to be positioned is located on the ground, and is covered periodically by the shadow; and the light source flashes periodically, and the cycle of the periodic flashing is the same as the cycle of rotation of the blade;

(2) detecting a light signal of the target to be positioned:

detecting light signal intensity received by the target to be positioned through a photosensitive sensor; within the time of one cycle of rotation of the blade, when the photosensitive sensor detects that the light signal intensity changes due to the periodic flashing of the light source, denoting the time as a reference time, and denoting a straight line where a projection of a diamond long diagonal of the blade on the ground at the reference time is located as a reference line;

(3) positioning the position of the target to be positioned:

according to changes of the light signal intensity with the periodic light pattern detected by the photosensitive sensor, judging a distance ρ from the target to be positioned to the connecting line between the center of the light source and the center of the blade, and a deflection angle θ of the target to be positioned relative to the reference line.

As a further optimization of the present invention, if the cycle of rotation of the blade is denoted as T, and within the time of one cycle of rotation of the blade, the duration during which the light signal intensity detected by the photosensitive sensor keeps weak light intensity due to the periodic light pattern is τ, the distance ρ from the target to be positioned to the connecting line between the center of the light source and the center of the blade satisfies: ρ=R(1−2πτ/T/D)×h/H, wherein h is a distance from the center of the light source to the center of the blade, and H is a distance from the center of the light source to the ground.

As a further optimization of the present invention, if the cycle of rotation of the blade is denoted as T, within the time of one cycle of rotation of the blade, the time at which the light signal intensity detected by the photosensitive sensor changes from strong to weak due to the periodic light pattern is denoted as a changing time, and the time at which the changing time lags behind the reference time is denoted as T', the angle θ of the target to be positioned relative to the reference line satisfies: θ=2πT'/T.

As a further optimization of the present invention, the light source is an LED point light source.

Through the above technical solutions conceived in the present invention, compared with the prior art, by deploying a device which can generate a dynamic light pattern with a particular regularity, multiple targets to be positioned that only need photosensitive sensors can achieve high-precision self-positioning. Therefore, the light pattern-based indoor positioning method has the following advantages such as high positioning precision, a stable positioning result, a low deployment cost, a simple requirement for hardware of the targets to be positioned, being capable of positioning more targets at the same time, and easy expansion of the positioning range.

The present invention, by making use of rotation of a blade in a particular shape, causes a projection of a positioning area to change according to a particular regularity, that is, generate a dynamic light pattern; a target to be positioned judges a distance from an axis of rotating projection by detecting a changing regularity of the light pattern, and then judges a direction relative to the axis of rotating projection according to rotating phase indication information generated by turn-on and turn-off (that is, flashing) of the light source, so as to determine its own position.

DETAILED DESCRIPTION

In order to make the objectives, technical solutions and advantages of the present invention more comprehensible, the present invention is further described below in detail with reference to the accompanying drawings and embodiments. It should be understood that specific embodiments described herein are merely used to explain the present invention, but are not used to limit the present invention. In addition, technical features involved in each implementation manner of the present invention described below can be combined with each other as long as they do not conflict with each other.

Embodiment 1

Figure 2:
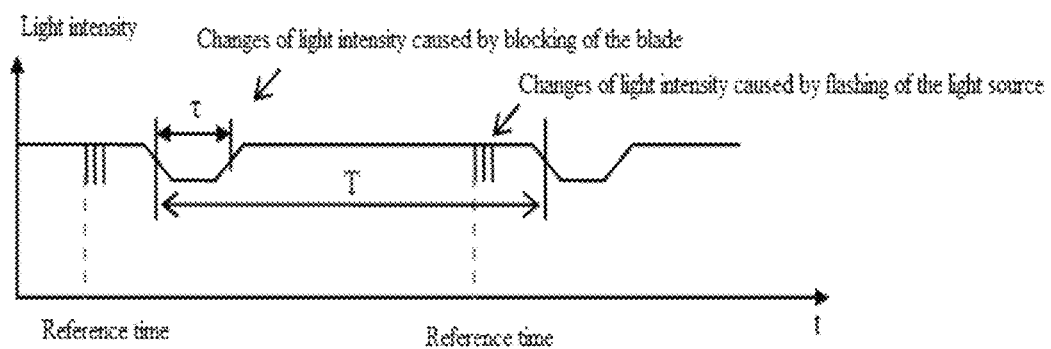
FIG. 2 is an example of changes of light intensity detected by a photosensitive sensor caused by a blade's blocking a light source periodically.

A light pattern-based indoor positioning method, including the following steps of:

(1) setting a light pattern transmitting device:

the light pattern transmitting device including a light source, a blade and a motor, wherein the blade is connected with the motor, the motor drives the blade to make the blade rotate at a constant speed around a rotating shaft of the blade; a straight line where the rotating shaft of the blade is located passes through the center of the light source, and the rotating shaft is perpendicular to the ground; light emitted by the light source is blocked by the blade to form a shadow on the ground, and the shadow rotates periodically along with the blade to form a periodic light pattern; on a ground area covered periodically by the shadow, within the time of one cycle of rotation of the blade, the duration during which points on the ground area at different distances from the rotating shaft of the blade are kept to be covered by the shadow due to the periodic light pattern is different; a target to be positioned is located on the ground, and is covered periodically by the shadow; and the light source flashes periodically, and the cycle of the periodic flashing is the same as the cycle of rotation of the blade (as shown in FIG. 2);

(2) detecting a light signal of the target to be positioned:

detecting light signal intensity received by the target to be positioned through a photosensitive sensor; within the time of one cycle of rotation of the blade, when the photosensitive sensor detects that the light signal intensity changes due to the periodic flashing of the light source, denoting the time as a reference time, and denoting a projection of a straight line passing through any two points on the blade on the ground at the reference time as a reference line, wherein the straight line passing through any two points on the blade and the straight line where the rotating shaft is located intersect with but do not coincide with each other;

(3) positioning the position of the target to be positioned:

according to changes of the light signal intensity with the periodic light pattern detected by the photosensitive sensor, judging a distance ρ from the target to be positioned to the rotating shaft of the blade, and a deflection angle θ of the target to be positioned relative to the reference line.

If the cycle of rotation of the blade is denoted as T, within the time of one cycle of rotation of the blade, the time at which the light signal intensity detected by the photosensitive sensor changes from strong to weak due to the periodic light pattern is denoted as a changing time, and the time at which the changing time lags behind the reference time is denoted as T', the angle θ of the target to be positioned relative to the reference line satisfies: θ=2πT'/T.

Embodiment 2

Figure 1:
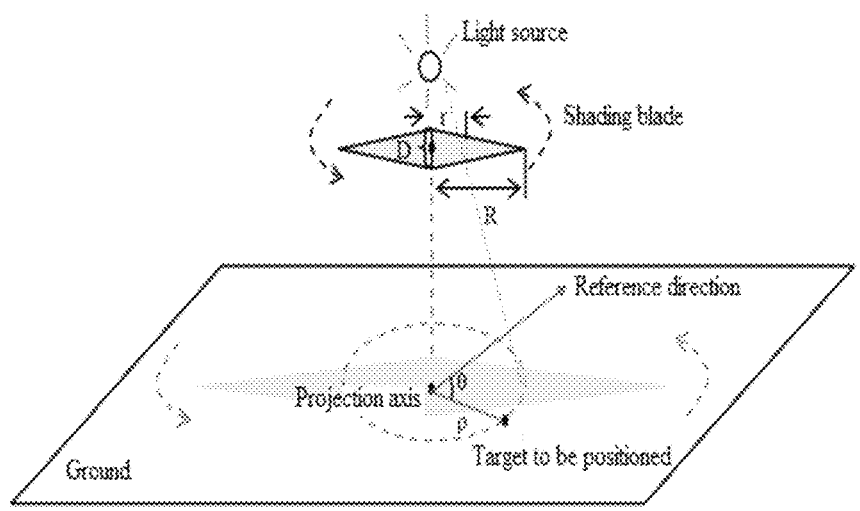
FIG. 1 is an example of a transmitting device that generates a simple light pattern and a light pattern thereof projected on the ground.

By taking a diamond blade as an example, FIG. 1 illustrates a light pattern transmitting device based on simple triangular double blades, the width of the triangular blades is D, and the height is R. The blades in the light pattern transmitting device rotate at a constant speed, and project a periodic light pattern on the ground. In addition, each time the blades rotate to a particular direction, the light pattern transmitting device controls the light source to be turned on and turned off several times according to a certain regularity, to be used as an indication when the blades rotate to a reference direction.

A target to be positioned somewhere on the ground, through a photosensitive sensor thereof, detects a regularity of changes of light intensity caused by the blades' blocking the light source periodically and turn-on and turn-off of the light source, as shown in FIG. 2.

Next, analysis is conducted according to the following steps:

1) The target to be positioned extracts the regularity of changes of light intensity caused by turn-on and turn-off of the light source, to determine a time at which the blades rotate to the reference direction.

2) The target to be positioned, by detecting a cycle of changes of light intensity caused by the blades' blocking the light source periodically, calculates an angular speed $2\pi/T$ at which the blades rotate. The target to be positioned detects the duration during which the light intensity becomes weak caused by blocking the light source by a single blade (that is, a diamond blade is made up of two triangular blades, and a single blade is one triangular blade therein) within a current cycle. According to the angular speed at which the blade rotates, on the plane of the target to be positioned, it is obtained through calculation that the arc length (which can be approximated as the width) of a part on the blade which blocks the target to be positioned is $2\pi\tau/T$. The target to be positioned, according to the shape of the blade and $2\pi\tau/T$, judges that a distance r from the part on the blade which blocks the target to be positioned to the center of the blade. As, in the example, the blade is a simple triangle, $r=R(1-2\pi\tau/T/D)$. Further, the target to be positioned, according to a distance h from a point light source to the center of the blade and a distance H from the point light source to the ground, can obtain a distance from the target to be positioned to the axis of rotating projection $\rho=r*h/H=R(1-2\pi\tau/T/D)*h/H$.

A derivation process of the above formula is as follows: the arc length $2\pi\tau/T$ of the part on the blade which blocks the target to be positioned is approximated as the width, and a ratio of the width to the length of the short diagonal of the blade (that is, $2\pi\tau/T/D$) is equal to a distance from the blocking part of the blade to the end of the long diagonal of the blade divided by a distance R from the center of the blade to the end of the long diagonal. Therefore, the distance from the blocking part of the blade to the end of the long diagonal of the blade is $R*2\pi\tau/T/D$. It can be thus obtained that a distance r from the center of the blade to the blocking part of the blade is $R-R*2\pi\tau/T/D=R(1-2\pi\tau/T/D)$. If a distance from the point light source to the center of the blade is set as h and a distance from the point light source to the ground is H, a distance from the target to be positioned to the axis of rotating projection is $\rho=r*h/H=R(1-2\pi\tau/T/D)*h/H$.

3) The target to be positioned judges the position on a period signal of changes of light intensity caused by the blade's blocking the light source periodically at a reference direction time, accordingly calculates the time T' of a time, when the blade begins to block the target to be positioned in each cycle, which lags behind relative to the reference direction time, and calculates according to T'/T an angle $\theta$ of the target to be positioned relative to a direction of a projection axis and a reference direction, as shown in FIG. 1. The position of the target to be positioned is determined by polar coordinates $(\rho, \theta)=(R(1-2\pi\tau/T/D)*h/H, 2\pi T'/T)$ which takes the projection axis as the origin.

To ensure the precision, the light source in the present invention is a point light source, which generally uses a single LED lamp, and the power of the light source is not lower than 1 W. The height of the point light source off the ground determines a circular range within which the ground detects the light pattern. The radius of the range is $\tau_{max}=R*h/H$, herein R is equivalent to the equivalent maximum radius of the blade, wherein R/h is generally less than 2. The length of the short diagonal of the diamond blade determines an undetectable range of the ground directly below the point light source, which has to be less than the diameter of a small motor below the blade. The cycle T of periodic changes of the light is not higher than 40 ms, that is, the rotating speed of the motor is not lower than 25 r/s. The value of the rotating speed of the motor is preferably a value which is a non-integer multiple of 50 (if the device is used in another region, as a local alternating current frequency may vary, it should be avoided that the rotating speed (r/s) of the motor is a value of an integer multiple of the local alternating current frequency (Hz)). The duration ti during which light intensity of a target to be measured is weak light intensity is not lower than 2 times of a sampling interval of the photosensitive sensor on the target to be positioned.

The blade in the present invention may also be in a shape of a triangle, an oval or the like, and the flashing of the light source in the present invention may also be a situation where the light intensity becomes stronger from normal intensity.

It should be easily understood by persons skilled in the art that the above are merely preferred embodiments of the present invention, but are not used to limit the present invention; any modification, equivalent replacement, improvement and the like made within the spirit and principle of the present invention should be included in the protection scope of the present invention.

The invention claimed is:

1. A light pattern-based indoor positioning method, comprising the following steps of:
   (1) setting a light pattern transmitting device:
   the light pattern transmitting device comprising a light source, a blade and a motor, wherein
   the blade is connected with the motor, the motor drives the blade to make the blade rotate at a constant speed around a rotating shaft of the blade; a straight line where the rotating shaft of the blade is located passes through the center of the light source, and the rotating shaft is perpendicular to the ground; light emitted by the light source is blocked by the blade to form a shadow on the ground, and the shadow rotates periodically along with the blade to form a periodic light pattern; on a ground area covered periodically by the shadow, within the time of one cycle of rotation of the blade, the duration during which points on the ground area at different distances from the rotating shaft of the blade are kept to be covered by the shadow due to the periodic light pattern is different; a target to be positioned is located on the ground, and is covered periodically by the shadow; and
   the light source flashes periodically, and the cycle of the periodic flashing is the same as the cycle of rotation of the blade;
   (2) detecting a light signal of the target to be positioned:
   detecting light signal intensity received by the target to be positioned through a photosensitive sensor; within the time of one cycle of rotation of the blade, when the photosensitive sensor detects that the light signal intensity changes due to the periodic flashing of the light source, denoting the time as a reference time, and denoting a projection of a straight line passing through any two points on the blade on the ground at the reference time as a reference line, wherein the straight line passing through any two points on the blade and the straight line where the rotating shaft is located intersect with but do not coincide with each other;

(3) positioning the position of the target to be positioned:
according to changes of the light signal intensity with the periodic light pattern detected by the photosensitive sensor, judging a distance $\rho$ from the target to be positioned to the rotating shaft of the blade, and a deflection angle $\theta$ of the target to be positioned relative to the reference line.

2. The light pattern-based indoor positioning method according to claim 1, wherein, if the cycle of rotation of the blade is denoted as T, within the time of one cycle of rotation of the blade, the time at which the light signal intensity detected by the photosensitive sensor changes from strong to weak due to the periodic light pattern is denoted as a changing time, and the time at which the changing time lags behind the reference time is denoted as T', the angle $\theta$ of the target to be positioned relative to the reference line satisfies: $\theta=2\pi T'/T$.

3. A light pattern-based indoor positioning method, comprising the following steps of:

(1) setting a light pattern transmitting device:
the light pattern transmitting device comprising a light source, a blade and a motor, wherein the blade is preferably a diamond, the plane where the diamond is located is parallel to the ground, the length of the long diagonal of the diamond is denoted as 2×R, and the length of the short diagonal of the diamond is denoted as D;

the motor drives the blade to make the blade rotate at a constant speed, a connecting line between the center of the light source and the center of the blade is perpendicular to the ground, light emitted by the light source is blocked by the blade to form a shadow on the ground, and the shadow rotates periodically along with the blade to form a periodic light pattern; a target to be positioned is located on the ground, and is covered periodically by the shadow; and the light source flashes periodically, and the cycle of the periodic flashing is the same as the cycle of rotation of the blade;

(2) detecting a light signal of the target to be positioned:
detecting light signal intensity received by the target to be positioned through a photosensitive sensor; within the time of one cycle of rotation of the blade, when the photosensitive sensor detects that the light signal intensity changes due to the periodic flashing of the light source, denoting the time as a reference time, and denoting a straight line where a projection of a diamond long diagonal of the blade on the ground at the reference time is located as a reference line;

(3) positioning the position of the target to be positioned:
according to changes of the light signal intensity with the periodic light pattern detected by the photosensitive sensor, judging a distance $\rho$ from the target to be positioned to the connecting line between the center of the light source and the center of the blade, and a deflection angle $\theta$ of the target to be positioned relative to the reference line.

4. The light pattern-based indoor positioning method according to claim 3, wherein, if the cycle of rotation of the blade is denoted as T, and within the time of one cycle of rotation of the blade, the duration during which the light signal intensity detected by the photosensitive sensor keeps weak light intensity due to the periodic light pattern is $\tau$, the distance $\rho$ from the target to be positioned to the connecting line between the center of the light source and the center of the blade satisfies: $\rho=R(1-2\pi\tau/T/D)\times h/H$, wherein h is a distance from the center of the light source to the center of the blade, and H is a distance from the center of the light source to the ground.

5. The light pattern-based indoor positioning method according to claim 3, wherein, if the cycle of rotation of the blade is denoted as T, within the time of one cycle of rotation of the blade, the time at which the light signal intensity detected by the photosensitive sensor changes from strong to weak due to the periodic light pattern is denoted as a changing time, and the time at which the changing time lags behind the reference time is denoted as T', the angle $\theta$ of the target to be positioned relative to the reference line satisfies: $\theta=2\pi T'/T$.

6. The light pattern-based indoor positioning method according to claim 3, wherein the light source is an LED point light source.

* * * * *